(12) United States Patent
Markham et al.

(10) Patent No.: US 6,939,937 B2
(45) Date of Patent: *Sep. 6, 2005

(54) MOLD INHIBITOR INTEGRATED WITHIN A MATRIX AND METHOD OF MAKING SAME

(76) Inventors: Joseph P. Markham, 12094 W. 75th Pl., Arvada, CO (US) 80005; Thomas Kieth Martin, 104 Crestway Ter., Amarillo, TX (US) 79106

( * ) Notice: Subject to any disclaimer, the term of this patent is extended or adjusted under 35 U.S.C. 154(b) by 101 days.

This patent is subject to a terminal disclaimer.

(21) Appl. No.: 10/431,488

(22) Filed: May 6, 2003

(65) Prior Publication Data

US 2004/0224060 A1 Nov. 11, 2004

(51) Int. Cl.[7] .................................................. C08G 2/00
(52) U.S. Cl. ............................ 528/3; 524/27; 424/661; 424/484; 424/488; 424/718
(58) Field of Search ................................ 528/3; 514/47

(56) References Cited

U.S. PATENT DOCUMENTS

| | | | |
|---|---|---|---|
| 3,119,691 A | 1/1964 | Ludington et al. | 99/2 |
| 3,284,211 A | 11/1966 | Williams | 99/2 |
| 3,467,525 A | 9/1969 | Hale et al. | 99/2 |
| 3,665,998 A | 5/1972 | Nowak | 164/76 |
| 3,725,324 A * | 4/1973 | Cummisford | 524/47 |
| 3,754,961 A | 8/1973 | Ueno et al. | 117/16 |
| 3,808,340 A | 4/1974 | Palmer | 426/92 |
| 3,882,255 A | 5/1975 | Gorham, Jr. et al. | 426/235 |
| 3,958,009 A * | 5/1976 | Lepore et al. | 514/557 |
| 4,000,319 A | 12/1976 | Eichelburg | 426/2 |
| 4,039,687 A | 8/1977 | Weyn | 426/62 |
| 4,104,407 A | 8/1978 | Stringer et al. | 426/99 |
| 4,143,169 A | 3/1979 | Skoch et al. | 426/307 |
| 4,145,447 A | 3/1979 | Fisher et al. | 426/72 |
| 4,162,336 A | 7/1979 | Brown, Jr. et al. | 426/623 |
| 4,229,485 A | 10/1980 | Brown et al. | 426/305 |
| 4,388,302 A * | 6/1983 | Ecanow | 424/672 |
| 4,410,551 A | 10/1983 | Comer | 426/99 |
| 4,454,804 A | 6/1984 | McCulloch | 99/348 |
| 4,592,913 A | 6/1986 | Hara | 426/104 |
| 4,617,328 A | 10/1986 | Liu | 523/122 |
| 4,659,583 A | 4/1987 | Hashimoto et al. | 426/629 |

(Continued)

OTHER PUBLICATIONS

Product Brochure for Biofoam packaging material: 4 pages, Biofoam Corporation, 918 South Park Lane, Tempe Arizona 85281.
Explanation of Reference AA (Product Brochure for Biofoam packaging material).
Wharton et al.; "Temporal synthesis and radiolabelling of the sorghum 3–deoxyanthocyankidin phytoalexins and the anthocyanin, cyanidin 3–dimalonyl glucoside"; RESEARCH New Phtol. (2000); vol. 145; pps. 457–469.

(Continued)

*Primary Examiner*—James J. Seidleck
*Assistant Examiner*—Irina S. Zemel
(74) *Attorney, Agent, or Firm*—Sheridan Ross P.C.

(57) ABSTRACT

A mold inhibitor integrated within a matrix and a method of making the same are disclosed. The matrix is preferably made of a processed sorghum grain, and preferably from hybrids of Milo. The grain is subjected to decortication and extrusion. Agents are added to the decorticated Milo prior to extrusion. The agents may be anti-fungal agents or anti-microbial agents. In use, the produced matrix is spread and placed upon a targeted area which requires either remediation or prevention of growth of fungus or microbes.

13 Claims, 1 Drawing Sheet

U.S. PATENT DOCUMENTS

| | | | |
|---|---|---|---|
| 4,713,250 A | 12/1987 | Tonyes et al. | 426/2 |
| 4,735,812 A | 4/1988 | Bryson et al. | 426/262 |
| 4,879,850 A | 11/1989 | Glassco et al. | 52/82 |
| 5,071,665 A | 12/1991 | Buckley et al. | 426/272 |
| 5,224,315 A | 7/1993 | Winter, IV | 52/309.8 |
| 5,373,674 A | 12/1994 | Winter, IV | 52/309.9 |
| 5,497,594 A | 3/1996 | Giuseppe et al. | 52/730.4 |
| 5,710,190 A | 1/1998 | Jane et al. | 521/102 |
| 5,713,526 A | 2/1998 | Martin et al. | 241/74 |
| 5,820,039 A | 10/1998 | Martin et al. | 241/7 |
| 5,858,436 A * | 1/1999 | Bompeix et al. | 426/321 |
| 5,894,029 A | 4/1999 | Brown et al. | 426/302 |
| 6,414,044 B2 | 7/2002 | Taylor | 521/65 |
| 6,433,034 B1 | 8/2002 | Leenslag et al. | 521/174 |

OTHER PUBLICATIONS

Nicholson et al,; "Phytoalexin synthesis by the sorghum mesocotyl in response to infection by pathogenic and non-pathogenic fungi"; Proc. Natl. Acad. Sci. USA. vol. 84, Aug. 1987 Applied Biology; pps. 5520–5524.

Host Defense: Sorghum Anthracnose Diseases; http://www.sorghumanthracnose.org/hostdef.html; 4 pages.

Wharton et al.; "Determination of the Temporal Synthesis of Sorghum Phytoalexins Using Photodiode Array–HPLC and Matdi–Mass Spectrometry"; http://www.bspp.org.uk/lcpp98/1.9/13.html; 2 pages.

* cited by examiner

MOLD INHIBITOR INTEGRATED WITHIN A MATRIX AND METHOD OF MAKING SAME

FIELD OF THE INVENTION

The present invention relates to the production of anti-microbial and anti-fungal materials, and more particularly, to a mold inhibitor integrated within a natural matrix, and a method of making the same.

BACKGROUND OF THE INVENTION

In the construction or building industry, it is known to incorporate various anti-microbial and anti-fungal agents within construction materials to thereby enhance the ability of the construction materials to inhibit undesirable growth of microbes or mold. Particularly in humid and wet climates, microbial and mold growth in building materials can cause many health related problems.

One example of a reference disclosing building materials which may incorporate such anti-fungal/microbial agents is the U.S. Pat. No. 4,879,850. The construction material disclosed therein includes a strawboard made of cereal stocks, such as rice, wheat, rye, oats and barley, the strawboard being manufactured through an extrusion process. Anti-fungal agents, anti-bacterial agents, mold inhibitors, rodenticides and the like may be added as ingredients to the strawboard composition, or may be applied as coatings.

A reference disclosing a foamed material which may be used for insulation and which incorporates an anti-microbial agent is the U.S. Pat. No. 5,710,190. The insulation material is a soy protein-based thermoplastic composition. The composition is made of soy protein combined with a foaming agent, an organic plastisizing agent, an aqueous medium such as water, and additives as desired. Articles formed from the composition have a foamed, cellular structure. The thermoplastic compositions are prepared by mixing together the components, and then molding the components by a compression molding process. Alternatively, the composition may be extruded to produce pellets. The anti-microbial agents disclosed, such as fungicides or bactericides, include sodium salts of propionic or sorbic acid, sodium diacetate, parabens, vinegar, monocalcium phosphate, or lactic acid.

In the construction industry, one particularly important health issue has been raised which involves remediation and prevention of fungal growth, particularly in basements or crawl spaces. Depending upon the particular type of construction, and the particular geographic area in which the building is found, crawl spaces, basements, or other areas within the building may provide suitable environments for fungal and/or microbial growth. Oftentimes, basements and crawl spaces are not adequately ventilated which contributes to growth of mold/microbes. In new construction, crawl spaces are often not ventilated until final steps in the construction which allows mold to grow and colonize to unacceptable levels. The mold may quickly spread to other areas within the building. This mold poses a health hazard to many individuals.

Current methods to remediate such mold problems may be expensive and structurally intrusive. In some cases, it may be necessary to remove and replace construction materials that have been sufficiently invaded with the mold or microbe.

Therefore, it can be seen that there is a need to prevent mold or microbial growth and to remediate buildings which have such mold/microbial problems.

SUMMARY OF THE INVENTION

It is one object of the present invention to provide anti-fungal materials which may be used to prevent and remediate the growth of mold. It is yet another object of the present invention to provide a matrix or carrier which may incorporate an anti-fungal agent, the matrix or carrier being inexpensive, and easy to manufacture. It is yet another object of the present invention to provide an anti-fungal material which may be easily introduced into crawl spaces or other confined areas, and which may be easily spread over a designated area. It is yet another object of the invention to provide a natural matrix or carrier, and one that is also hydrophobic.

The product of the present invention may be defined as a mold inhibitor which is integrated within a matrix. The matrix is preferably manufactured from Milo seeds which have been decorticated resulting in berry and berry particulates which may then be exposed to extrusion. An anti-fungal agent or inhibitor may be directly added to the decorticated Milo prior to extrusion.

Sorghum Vulgare is a domesticated plant well known to man. It has been hybridized since early Egyptian years and is very diversified in its hybrid state. Varieties commonly referred to as Milo have few if any uses other than for animal feed. Sorghum Vulgare is widely used in the United States as a less expensive feed grain substituted for corn or wheat. Other parts of the world, particularly Africa and Asia use sorghum for flour and human food. In the United States, Milo is a particular group of hybrids that is a very different type of cereal grain as compared to sorghum which is grown in other parts of the world.

In the present invention, it has been found that Milo is a cereal grain which may be extruded into a matrix or carrier which then may be combined with an anti-fungal agent. This matrix may be introduced into confined spaces within man-made structures to prevent and to remediate the growth of mold or other fungal growths.

The particular size and density of the extruded Milo matrix pieces may be adjusted to best fit the type of space which is to be remediated. The extruded matrix may be a light, puffy cellular mass, incorporating the anti-fungal agent, or the extrusion process can produce a more dense, nugget like or bead like product which incorporates the anti-fungal agent. The size and density of the product can be adjusted by choosing a particular pressure and temperature of the extrusion process. Additionally, adjusting the moisture content of the Milo will also adjust the particular size and density of a product which is produced in the extrusion.

Types of anti-fungal agents which are contemplated within the present invention include, but are not limited to, chlorine pellets, sodium nitrate, and garlic extract.

Milo has a number of advantages for use as a matrix in providing an anti-fungal agent. As mentioned above, Milo is naturally hydrophobic. Therefore, the matrix may be used within wet or damp spaces, and the Milo matrix will not easily degrade. Milo is also flame resistant and will not pose an additional fire hazard to building structures. Milo in its extruded state is odorless, and has excellent storage characteristics which allow the Milo matrix to be stored for long periods of time even prior to use.

In addition to anti-fungal agents, it is also contemplated that the Milo matrix of the present invention be combined with anti-microbial agents to include anti-bacterial agents and others.

In accordance with the method of the present invention, a method of making the milo matrix is disclosed. A desired stock of Milo grain is chosen, and the selected grain is cleaned and sized. A de-stoning operation may be incorporated to remove any hard material of like size and shape, such as small stones or pebbles. The Milo grain is then decorticated in one of several known methods of grain decorticating. The decortication removes the husks or hulls of the Milo seeds. Optionally, the remaining berry and berry particulates may be passed through a scourer to remove the fatty endogerm portion of the berries. Defatting of the berries can enhance the ability of the Milo grain to be extruded because fat can act as a lubricant in extrusion thereby degrading the ability of an extruder to produce a consistent matrix. In the extrusion, a bake-type extruder is used under preferred heat and pressure ranges. The product produced in the extrusion process can be defined as a matrix of Milo which carries an anti-microbial or anti-fungal agent. One final step which may be required in the process is to cure the matrix. Curing allows the matrix to achieve equilibrium in terms of moisture content.

Other features and advantages of the present invention will become apparent from a review of the following detailed description, taken in conjunction with the drawing which illustrates a preferred embodiment of the method of the present invention.

DETAILED DESCRIPTION

Figure 1:
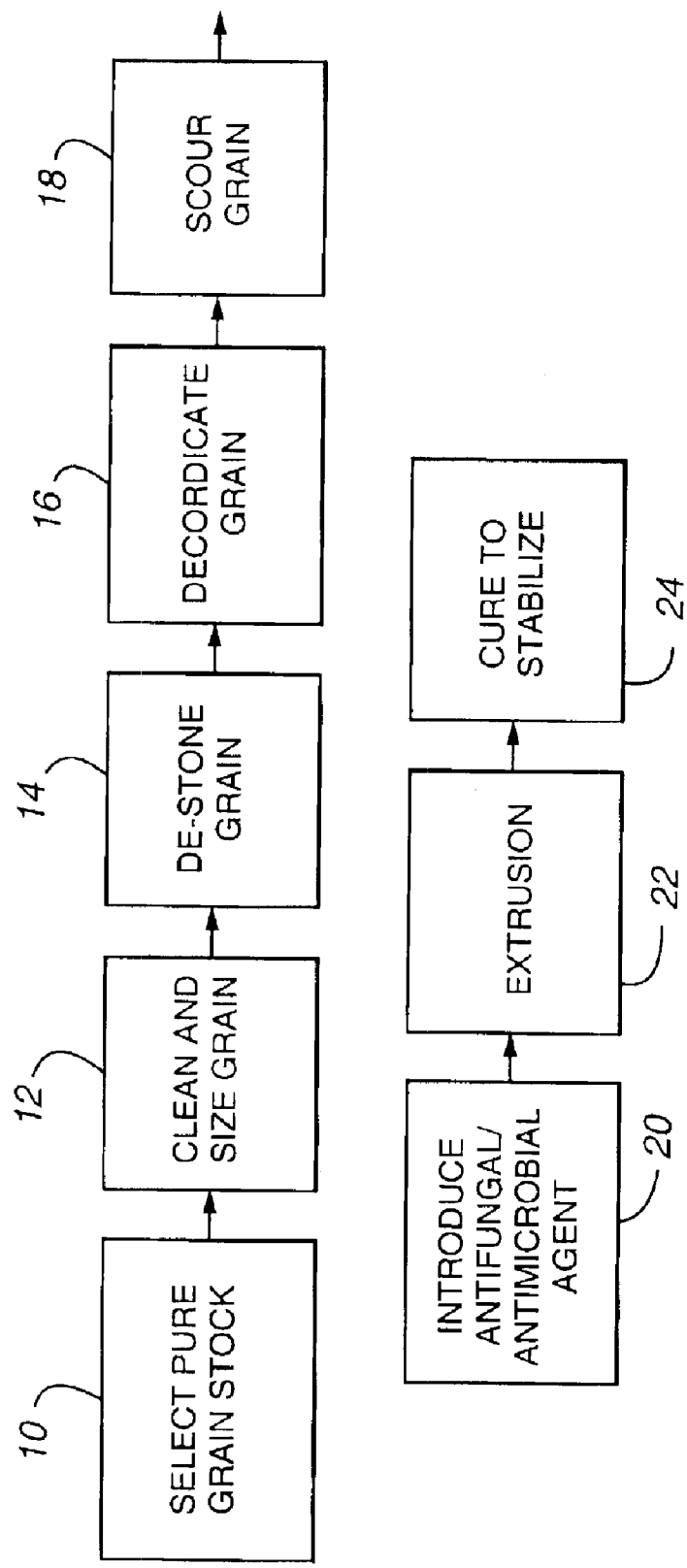
FIG. 1 is a flow chart showing the basic steps used in processing Milo grain according to the present invention to produce a Milo matrix which may be combined with anti-microbial or anti-fungal agents.

Referring to FIG. 1, basic steps in the method of making the matrix of the present invention are illustrated. In a first step at block 10, preferably, a pure stock of a Milo grain is selected. Although there is no specific hybrid of Milo which is required for the product and method of the present invention, it is desirable to choose a single pure stock grain because this pure stock grain is advantageous in creating consistency and repeatability of the extrusion process. Through testing, it has been found that a few particular hybrids of Milo are particularly adapted for extrusion. Three hybrid varieties which have shown great success include Triumph 65G, Asgrow Seneca, and Dekalb 5400. These three hybrid varieties are well known grain stocks for use in animal feed, and are commercially available in the U.S. Although these three hybrids are provided, it shall be understood that there may be a number of other hybrid varieties of Milo which are also adapted for consistent and repeatable extrusion.

The next step in the process shown at block 12 is to clean and size the Milo grain. Standard cleaning and sizing equipment may be used to process the grain at this step. For example, air/water streams may be used to clean the grain, and the grain may be passed through various sieves to obtain the desired grain size. In the present invention; however, there is no particular grain size required and multiple grain sizes may be used.

Shown at block 14 is the next step in the process which is an optional destoning operation to remove stones or other similar sized objects which may still remain in the grain after cleaning and sizing. Although a destoning operation is shown as a separate optional step, destoning can be incorporated within the cleaning and sizing of the grain at step 12.

The next step in the process is shown at block 16 which is the decortication of the Milo grain. Any one of several methods of usual grain decortication may be used to decorticate the Milo. Two references which disclose methods for decorticating Milo and which have been found to be particularly effective are the methods described in the U.S. Pat. Nos. 5,713,526 and 5,820,039. These two references are incorporated herein by reference for purposes of disclosing basic methods by which Milo grain may be decorticated.

The next step in the method is shown at block 18 which is an optional step of scouring the grain to remove fatty oils or lipids. In order to enhance the consistency and repeatability of the extrusion process, the fatty endogerm of the Milo may be removed because this fatty portion of the grain tends to act as a lubricant through the extrusion die thereby degrading extruder operation. Well known grain scouring processes may be used to remove the fatty endogerm from the Milo grain. Although scouring is discussed as a step in the basic method, it shall be understood that scouring is not necessarily required as it may be desirable in some circumstances to have certain levels of fat within the matrix. Additionally, scouring may be eliminated to simplify the overall production process.

The next step in the method is shown at block 20 which involves the introduction of a desired anti-fungal/anti-microbial agent to the processed Milo. The Milo and agent when combined may be referred to as a grain mix. There are a number of anti-fungal/anti-microbial agents which are contemplated within the present invention which may be used for inhibiting mold growth, or inhibiting growth of microbes. Examples of these agents include, but are not limited to, chlorine, sodium nitrate, and garlic extract. There are at least two natural mold inhibitors which are actually found within the Milo grain itself. In red Milo, the major pigments of this sorghum are apigeninidin and luteolinidin. These pigments are found in the hulls of the sorghum grain. Therefore, it is also contemplated within the present invention to recover the hulls of the grain which are removed during decortication, and then to process the hulls to extract the apigeninidin and luteolinidin. These removed pigments can then be added back to the decorticated grain prior to extrusion and used as the anti-fungal agents.

In order to provide an extrudable mixture, it is preferable to maintain the Milo at or around 16% moisture content prior to extrusion. Accordingly, an amount of water must be added to the decorticated Milo prior to extrusion. Depending upon the type of agent which is added to the decorticated Milo, a lesser or greater amount of water must be added to bring the moisture content of the Milo grain mix to preferably around 16%.

It may be desirable to mechanically mix the grain mix in a bin which will then meter the grain mix into the extrusion machine. Mechanical mixing helps to ensure uniform dispersion of the added agent.

The next step in the method is illustrated at block 22 which involves extrusion of the Milo grain mix. Through testing, it has been found that extrusion can be achieved utilizing a bake-type extruder which exposes the grain mix to heat in the range of about 325° F. to about 400° F., and pressure in the range of between about 1500 and about 2000 psi. The particular shape of the die used in the extruding machine may be adapted to produce a matrix of a desired shape. One example of a die could include the use of a die having a round shaped hole with a diameter of approximately 0.120 of an inch. The cutting mechanism used in the extruding machine could be adapted for cutting the extrudate to a length of approximately three-quarters of an inch. The resulting extruded product can be of different sizes and densities. For example, if a particularly small enclosed space must be remediated by introduction of the matrix, it may be desirable to provide the matrix in a more dense extrudate. Accordingly, the extrudate could have a smaller size and a nugget-like consistency. If the area to be remediated had not yet developed fungal or microbial problems and the purpose of introducing the matrix was primarily for prevention, then it may be adequate to provide the matrix in a larger sized, lighter, puffier extrudate. The amount of the anti-fungal/antimicrobial agent in the denser, nugget-like extrudate would be greater since more matrix is used per piece of extrudate while the amount of the anti-fungal/antimicrobial agent would be more dispersed within the lighter, puffy extrudate. Since the concentration of the anti-fungal/antimicrobial agent can vary depending upon the density of the extrudate, the extrudate can be tailored for each application. Of course, one could also simply vary the amount of the agent used when it is initially mixed with the decorticated Milo to provide the desired concentration of the agent in the matrix.

The last step of the method is shown at block 24 which contemplates curing the matrix product to thereby stabilize the product prior to storage and shipping. Depending upon the matrix produced, i.e., one which is either puffed or more dense, a certain amount of curing may be required to allow the matrix to reach equilibrium in terms of moisture content.

There are a number of advantages of utilizing a Milo matrix as a carrier for an anti-fungal and/or anti-microbial agent. First, the extruded Milo is naturally hydrophobic which therefore allows the Milo matrix to be used in damp or wet spaces for extended periods of time without substantial decay. Milo is a readily available grain source, and is relatively inexpensive compared to man made or artificial compositions. Another advantage as mentioned above is the ability to produce a matrix which has a variety of sizes and densities by simply altering the moisture content of the grain mix prior to extrusion. By altering the density, the concentration of the agent may also be adjusted.

The matrix of the present invention is easily deployed within many commercial structures by simply transporting the matrix to a desired location, and spreading the matrix within the desired space to be remediated or for prevention of mold and/or microbial growth. For prevention of mold, it has been found that spreading a layer of 3–6 inches of the lighter, puffier, matrix over the targeted area is adequate for preventing mold growth. For remediation of mold, it may be necessary to increase the depth of the spread matrix, and it may also be necessary to increase the density of the matrix at a particular location. As best understood, there are two primary ways in which the agent inhibits mold or microbial growth. The first is physical contact of the matrix with the area to be remediated. The second is production of an off-gas through sublimation of the additive into the atmosphere enclosed by the space to be remediated. For example, with chlorine, a certain amount of the solid chlorine will off gas producing a vapor which prevents mold growth. Of course, the concentration of the chlorine in the Milo matrix has to be controlled so that the off gas produced does not reach dangerous levels.

It may be necessary over time to add additional amounts of the matrix to the area to be remediated. As the agent continues to sublime or otherwise chemically break down, the concentration of the agent will diminish.

The present invention has been described with respect to a preferred embodiment; however, other changes and modifications may be made to the invention within the spirit and scope thereof.

What is claimed is:

1. A product especially adapted for inhibiting the growth of mold comprising:

a decorticated Milo grain seed mixed with an agent, the mixture being extruded to produce an extruded product having a substantially homogeneous mixture of Milo seeds and agent, the agent inhibiting the growth of mold upon contact with the agent; and said agent is selected from the group consisting of a solid chlorine mixture, sodium nitrate, and garlic extract.

2. A method of producing a product which inhibits the growth of mold, said method comprising the steps of:

decorticating a cleaned Milo grain;

introducing an agent having properties which inhibit mold growth to produce a grain mix;

extruding the grain mix to create an extrudate product having mold growth inhibiting properties; and wherein said agent is selected from the group consisting of a solid chlorine mixture, sodium nitrate, garlic extract and mixtures thereof.

3. A method, as claimed in claim 2, wherein:

moisture content of the grain mix prior to extrusion is about 16%.

4. A method, as claimed in claim 2, further comprising the step of: scouring the grain prior to extrusion to remove fatty endogerm of the grain.

5. A method, as claimed in claim 2, further comprising the step of: destoning the grain prior to the step of decorticating the grain.

6. A method, as claimed in claim 2, further comprising the step of:

altering the moisture content of the grain mix to thereby vary the density of the extrudate product.

7. A method, as claimed in claim 2, further comprising the step of:

curing the extrudate product.

8. A method, as claimed in claim 2, wherein:

increasing the moisture content of the grain mix prior to extrusion produces a smaller, denser extrudate, and lessening the moisture content of gram mix produces a larger, less dense extrudate.

9. A method of remediating mold growth in a man made structure, said method comprising the steps of:

providing a Milo matrix combined with an anti-fungal agent, said matrix being in the form of a plurality of extruded pieces; and spreading the pieces in the area to be remediated wherein the agent incorporated within the matrix inhibits mold growth by contact of the agent with the mold;

said matrix being produced by decorticating a Milo grain; and combining the agent with the decorticated grain to form a grain mix, and extruding the grain mix to produce the pieces, said agent including pigments processed from hulls removed from the decorticated grain, said pigments including apigeninidin and luteolinidin.

10. A method, as claimed in claim 9, wherein:

moisture content of grain mix prior to extrusion is about 16%.

11. A product, as claimed in claim 1, wherein:

said agent sublimes to create an off-gas vapor, the vapor further inhibiting mold growth.

12. A method, as claimed in claim 2, wherein:

said agent sublimes to create an off-gas vapor, the vapor further inhibiting mold growth.

13. A method, ass claimed in claim 9:

said agent sublimes to create an off-gas vapor, the vapor further inhibiting mold growth.

* * * * *

UNITED STATES PATENT AND TRADEMARK OFFICE
CERTIFICATE OF CORRECTION

PATENT NO. : 6,939,937 B2
DATED : September 6, 2005
INVENTOR(S) : Joseph P. Markham It is certified that error appears in the above-identified patent and that said Letters Patent is hereby corrected as shown below:

Column 6,
Line 40, delete "gram" and replace it with -- grain -- therein.

Signed and Sealed this

Eighth Day of November, 2005

JON W. DUDAS
*Director of the United States Patent and Trademark Office*